Figure 1A:
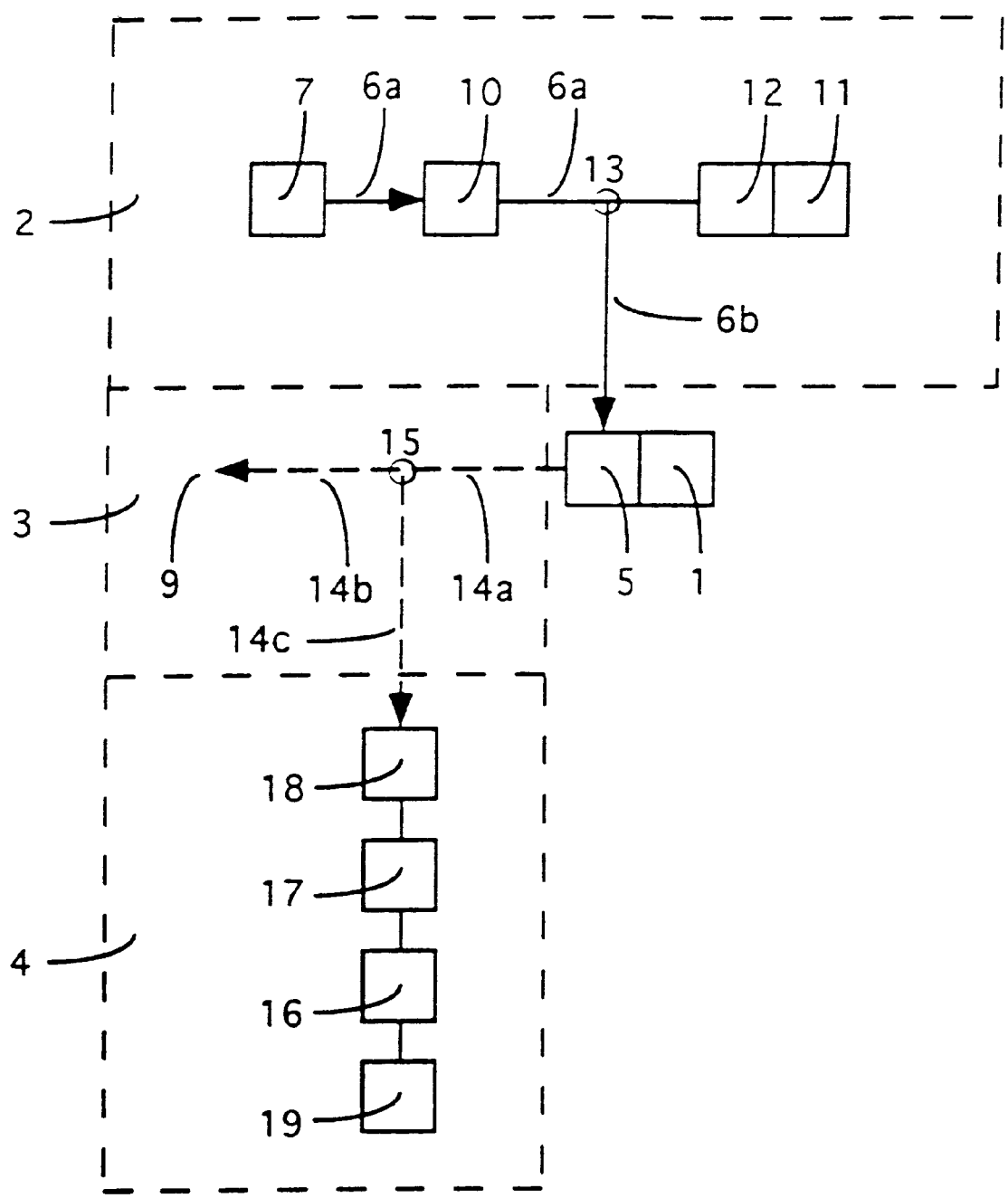

United States Patent
Alving et al.

[11] Patent Number: 5,922,610
[45] Date of Patent: *Jul. 13, 1999

[54] SYSTEM TO BE USED FOR THE DETERMINATION OF NO LEVELS IN EXHALED AIR AND DIAGNOSTIC METHODS FOR DISORDERS RELATED TO ABNORMAL NO LEVELS

[75] Inventors: Kjell Alving, Uppsala; Edward Weitzberg, Stockholm; Jan Lundberg, Djursholm, all of Sweden

[73] Assignee: Aerocrine AB, Danderyd, Sweden

[*] Notice: This patent issued on a continued prosecution application filed under 37 CFR 1.53(d), and is subject to the twenty year patent term provisions of 35 U.S.C. 154(a)(2).

[21] Appl. No.: 08/578,653
[22] PCT Filed: Jul. 4, 1994
[86] PCT No.: PCT/SE94/00659
  § 371 Date: Jan. 5, 1996
  § 102(e) Date: Jan. 5, 1996
[87] PCT Pub. No.: WO95/02181
  PCT Pub. Date: Jan. 19, 1995

[30] Foreign Application Priority Data

Jul. 6, 1993 [SE] Sweden ................................. 9302324
Apr. 20, 1994 [SE] Sweden ................................. 0401324

[51] Int. Cl.⁶ .......................... G01N 33/00; G01N 33/497
[52] U.S. Cl. .......................... 436/116; 436/181; 436/106; 422/83; 422/84; 422/93; 600/532
[58] Field of Search ..................... 436/116, 117, 436/118, 181; 128/716, 719; 422/83, 84, 90, 93, 98; 600/532

[56] References Cited

U.S. PATENT DOCUMENTS

| | | | |
|---|---|---|---|
| 5,081,871 | 1/1992 | Glaser | 73/863.23 |
| 5,396,882 | 3/1995 | Zapol | 128/200.14 |
| 5,425,374 | 6/1995 | Ueda et al. | 128/719 |
| 5,427,797 | 6/1995 | Frostell et al. | 424/434 |
| 5,447,165 | 9/1995 | Gustafsson | 128/719 |
| 5,485,827 | 1/1996 | Zapol et al. | 128/200.14 |
| 5,533,513 | 7/1996 | Ueda et al. | 128/719 |
| 5,573,005 | 11/1996 | Ueda et al. | 128/730 |
| 5,795,787 | 8/1998 | Silkoff et al. | |

FOREIGN PATENT DOCUMENTS

| | | |
|---|---|---|
| 91032433 | 11/1991 | Sweden . |
| 9305709 | 4/1993 | WIPO . |
| 9519173 | 4/1995 | WIPO . |

OTHER PUBLICATIONS

Acta Physiol Scand, "Allergen–induced airway obstruction in guinea–pigs is associated with changes in nitric oxide levels in exhaled air", Persson et al., 1993, 149, 461–466.

Application to the Research Committee at the Karolinksa Institute re: Application Human Testing (Sep. 7, 1992).

Application to the Research Committee at the Karolinksa Institute re: Application Human Testing (Dec. 23, 1992).

(List continued on next page.)

Primary Examiner—Long V. Le
Attorney, Agent, or Firm—Birch, Stewart, Kolasch & Birch, LLP

[57] ABSTRACT

The present invention is drawn to a system to be used for measuring NO levels in exhaled breathing air. The system comprises: (i) a face mask that tightly covers the nose and/or mouth of the individual that the mask is intended to be used on; (ii) an inlet unit for inhaled breathing air, (iii) an outlet unit for exhaled breathing air, (iv) a non-rebreathing valve through which inhaled and exhaled breathing air, respectively, passes, and (v) a measuring unit for NO connected to the outlet unit. The present invention furthers encompasses a method for the diagnosis in mammals of inflammatory conditions in the airways. The characteristic feature is that nitric oxide NO is measured in exhaled breathing air and a found abnormal level is taken as an indication of an inflammatory condition in the airways.

38 Claims, 4 Drawing Sheets

OTHER PUBLICATIONS

The Lancet, "Oxidant Activity in Expired Breath of Patients with Adult Respiratory Distress Syndrome", Baldwin, et al., Jan. 1, 1986, pp. 11–13.

Clinical Investigations in Critical Care, "Increased Hydrogen Peroxide in the Expired Breath of Patients with Acute Hypoxemic Respiratory Failure", Sznajdr, et al., Sep. 3, 1989 pp. 606–612.

Annals New York Academy of Sciences, "Hydrogen Peroxide in Human Breath and its Probable Role in Spontaneous Breath Luminescence", Williams, et al., 1982, pp. 478–483.

Biochemical and Biophysical Research Comm., "Endogenous Nitric Oxide is Present in the Exhaled Air of Rabbits, Guinea Pigs and Humans", Gustafsson, et al., vol. 181, No. 2, Dec. 16, 1991, pp. 852–857.

European Journal of Pharmacology, "Ethanol Can Inhibit Nitric Oxide Production", Persson, et al., 1992, pp. 99–100.

The FASEB Journal, "Measurement of Nitric Oxide in Biological Models", Stephen Archer, vol. 7, Feb. 1993, pp. 349–360.

SYSTEM TO BE USED FOR THE DETERMINATION OF NO LEVELS IN EXHALED AIR AND DIAGNOSTIC METHODS FOR DISORDERS RELATED TO ABNORMAL NO LEVELS

TECHNICAL FIELD

See the title. The invention is based on the fact, that for mammals, including humans, the level of nitric oxide (NO) in exhaled air of a mammal (including human) is indicative of certain disorders (diseases) including risks for acquiring them. This concept has now been shown useful at least for the diagnosis of inflammatory conditions of the airways, such as allergic asthma and rhinitis, and respiratory tract infections in humans, and Kartagener's syndrome. In particular infections in the lower respiratory tract may be diagnosed.

The measuring principle employed has indicated that NO production in normal human airways is restricted to the upper airways, specifically the nasal sinuses. It has also been shown that NO is produced in the stomach.

By airways is meant the conducting airways from the nostrils down to the respiratory bronchioles, containing mucosal tissue; and the nasal sinuses.

BACKGROUND

Over the last decade several approaches to the biological role of nitric oxide (NO) have been made. The synthesis of NO, which is catalysed by specialized NO synthases using L-arginine as a substrate, has now been shown to take place in many cell types (Nathan C., FASEB J. 6 (1992) 3051–64). The NO synthase exists in several isotypes that can be divided into two major classes: constitutive and inducible. The constitutive isotypes have been described in endothelial cells (Moncada S. et al., Pharmacol. Rev. 43 (1991) 109–42) and for instance in parasympathetic vasodilator nerves (Kummer W. et al., Neuroreport 3 (1992) 653–55). The inducible isotypes are found, after activation, in macrophages, neutrophils, endothelium, vascular smooth muscle (Moncada S. et al., Pharmacol. Rev. 43 (1991) 109–42) and even epithelium in the airways of asthmatic subjects (Springall et al., Am. Rev. Resp. Dis. 147 (1993) A515). The production of NO has so far been difficult to measure directly in vivo, although increases in the end-products nitrite and nitrate in plasma and urine can be used in some cases (Archer S., FASEB J. 7 (1992) 349–360). Recently, it was shown, however, that NO can be found in parts per billion (p.p.b.) levels in exhaled air of experimental animals and humans (Gustafsson L. E. et al., Biochem. Biophys. Res. Commun. 181 (1992) 852–7). Gustafsson et al have measured NO levels either by connecting a chemiluminescence detector to the exhaled air or by bubbling the exhaled air through a solution in which NO was chemically trapped. The human experiments appear to have been performed on one single individual who was allowed to inhale through the nose and exhale through the mouth. The relatively high NO level Gustafsson et al. have obtained compared to ours might be explained by passage of NO into the inhaled air when it passes through the nose. In a later publication Persson M. G. and Gustafsson L. E. have reported that ethanol intake will reduce NO formation as measured in exhaled air of rabbits (Eur. J. Pharmacol. 224 (1992) 99–100). Gustafsson L. E. himself has also suggested that measured NO levels in exhaled air may be used to check lung function (WO-A-9305709 and SE-91032433). The works of Gustafsson L. E. et al appears to be the closest prior art. During the priority year, data on increased levels of NO in exhaled air of asthmatic patients and decreased levels smokers have been published (Alving K. et al., Eur. Resp. J. 6 (October, 1993) 1368–70; Hamid Q. et al., Lancet 342 (December 1993) 1510–13; Karithonov S. A. et al., Lancet 343 (January 1994) 133–35; and Persson M. G et al., Lancet 343 (January 1994) 146–7.

THE OBJECTIVES OF THE INVENTION

A first and main objective of the invention is to provide utilities for earlier findings that endogenously produced nitric oxide (NO) can be detected in exhaled breathing air.

A second objective is to provide improved systems for the measurement of NO levels in exhaled air.

A third objective is improved and more reliable diagnostic methods for disorders (diseases) that are associated with an abnormal NO level in exhaled air. At the priority date, we had results indicating that the diseases concerned were related to inflammatory conditions (including risks to develop inflammation) in the airways, for instance allergic asthma and rhinitis, and infections in the lower airways. During the priority year, we have recognized that nasally derived NO originates from the nasal sinuses and that close to zero levels in nasally exhaled air are valuable indications of Kartagener's syndrome and, possibly, increased susceptibility for developing sinusitis. We have also shown that regurgitated air contains high levels of NO (formed in the stomach) and abnormal NO levels in regurgitated air is likely to be associated with gastric disturbances. We have, for instance, found that inhibition or lowering of gastric HCl production results in lowered NO levels and, thus, NO levels in regurgitated air may be used to monitor treatment with drugs inhibiting gastric acid secretion. Detection of increased level of NO in exhaled air (preferably orally exhaled air) may also be indicative of gastro-oesophagal reflux (abnormal leakage of gastric content including NO from the stomach). The inventive method is likely to also have a prognostic value.

Figure 1B:
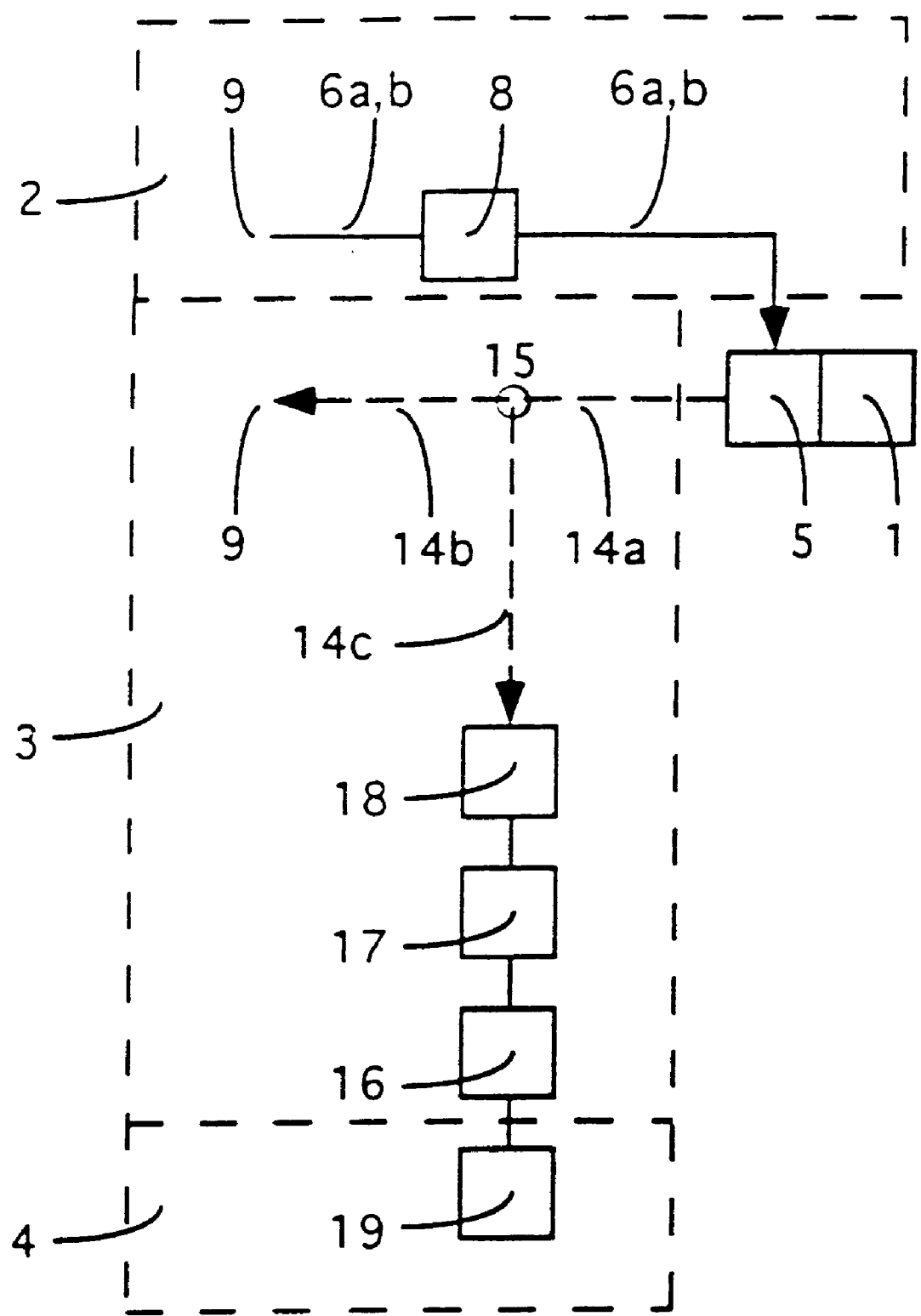

LEGENDS TO THE DRAWINGS:

FIGS. 1a and 1b illustrate a sampling and measuring system useful for measuring NO in nasally and/or orally exhaled air. In FIG. 1a the system utilises a pressurized source for breathing air essentially free of NO, and in FIG. 1b the source is ambient air. Corresponding functions in the figures are represented by the same numerals.

Figure 2:
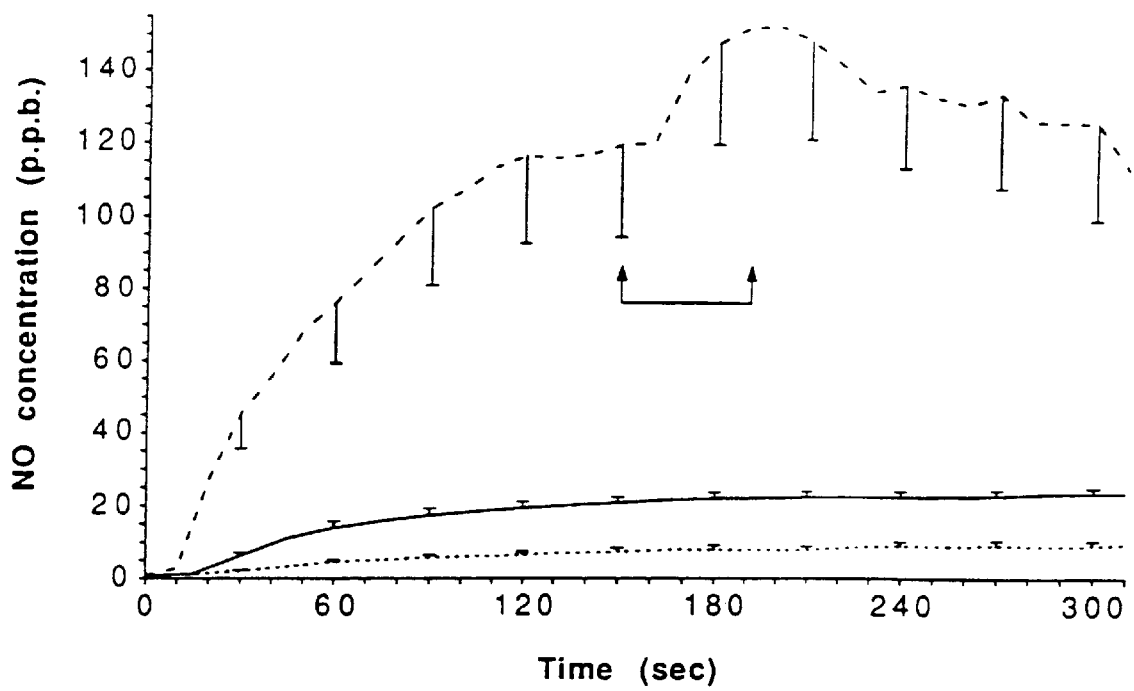

FIG. 2 shows levels of NO (p.p.b.) detected by chemiluminescence technique in exhaled air of control subjects during the first 5 min of oral breathing (dotted line), nasal breathing (solid line) or nasal ventilation with an airstream (broken line). The arrows indicate a period of holding the breath with the mouth closed. Data are given as mean ±SEM.

Figure 3A:
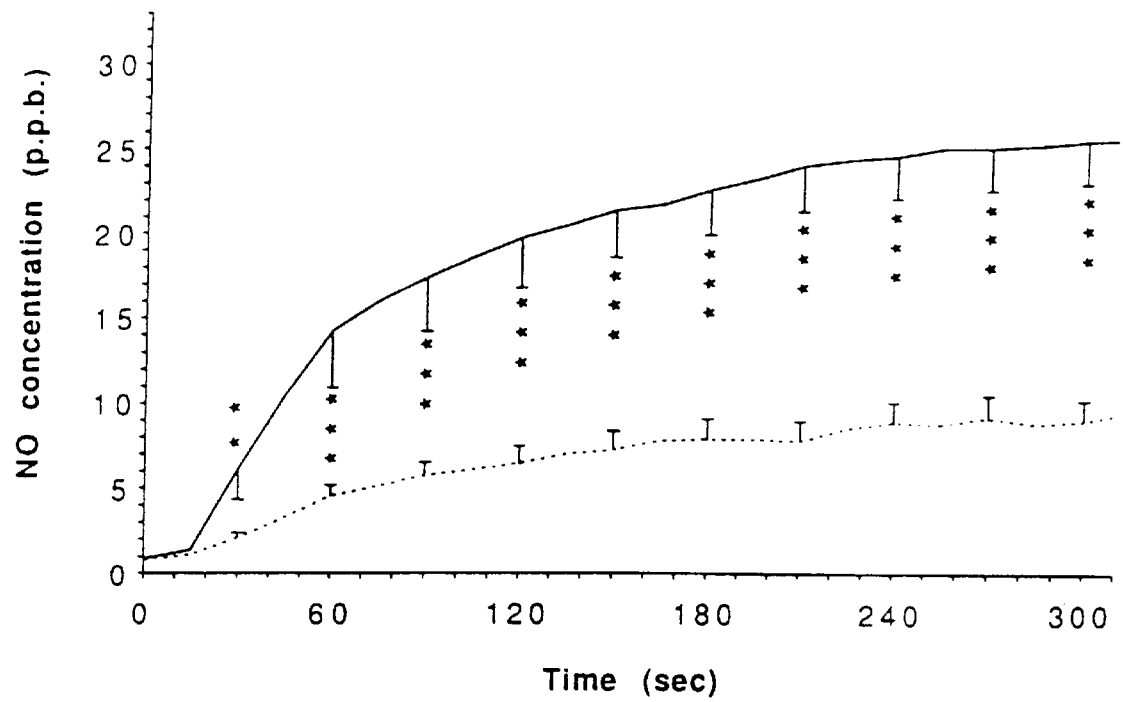
Figure 3B:
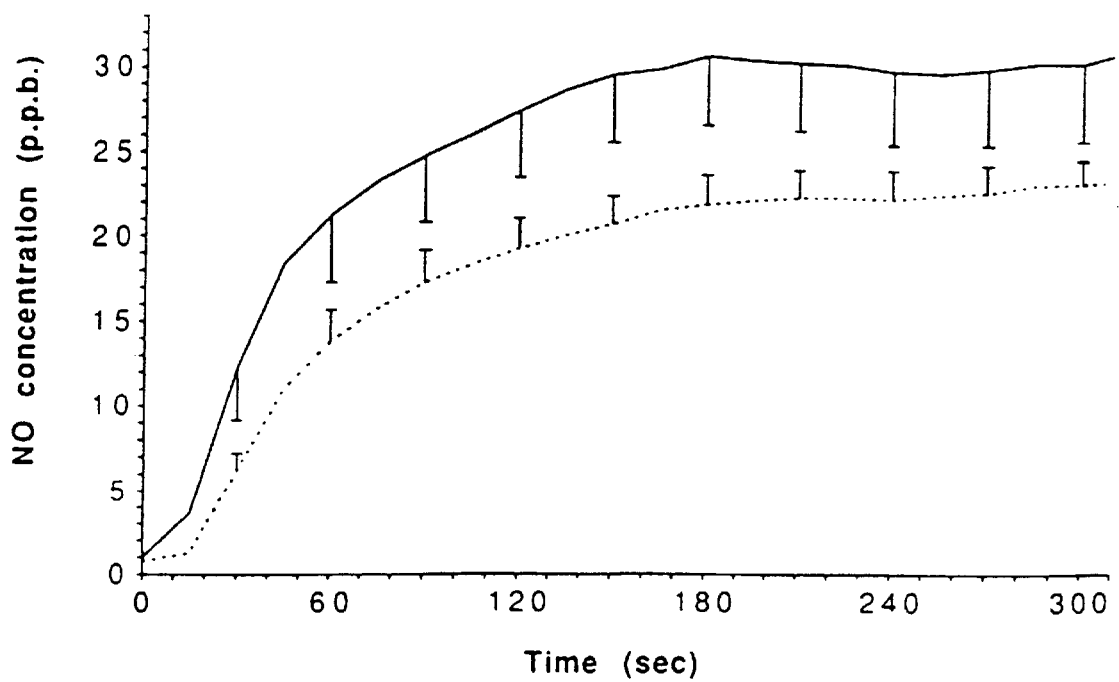

FIGS. 3a and 3b show detected levels of NO (p.p.b.) in exhaled air of controls (dotted line) and asthmatics (solid line) during the first 5 min of oral breathing (FIG. 3a), and nasal breathing (FIG. 3b). Data are given as mean ±SEM. $P<0.01$, *$P<0.001$ compared to controls (Mann-Whitney U-test).

THE INVENTION

System for measuring NO

The system of the invention for measuring NO in exhaled air is illustrated in FIG. 1 and comprises a face mask (1) that covers the mouth and/or the nose of the patient, an inlet unit (2) for inhaled air, an outlet unit (3) for exhaled air, and an NO measuring unit (4). The inlet and outlet units may be connected to each other via a non-rebreathing valve (5) that preferably is located on the face mask. As indicated the term "face mask" comprises also a mouth or nose piece through which it is possible to breath. A mouth piece is preferably used in combination with a nose clip. Conventional face masks and non-rebreathing valves may be used. In case the face mask used covers both the mouth and the nose there are advantages with transparent masks.

There are two main alternatives for the inlet unit (2). The first alternative (FIG. 1a) comprises tubings (6a,6b) connecting the mask (1) to a pressurized source (7) of breathing air, preferably containing less NO than the level found in normally exhaled air, for instance less than 1 p.p.b. NO. The second alternative (FIG. 1b) comprises tubings (6a,6b) that connect the mask (1) to ambient air (9), preferably via a filter (8) for removing NO. In order to support the mask (1) with a balanced smooth supply of air from the pressurized source (7), at least one of a flow meter (10) and an elastic air reservoir (11) linked to an outlet valve (12) should be connected in the given downstream order to the tubings (6a,6b) between the mask (1) and the pressurized air source (7). The flow meter (10) is used to adjust the air flow to match the test subject's air consumption. The air outlet valve (12), e.g. a Berner valve, is used to avoid the build up of pressure in the elastic reservoir (11) but also allowing the elastic reservoir (11) to be adequately inflated between breaths. The air outlet valve (12) should be set to open at a low pressure that will not force air through the non-rebreathing valve (5). Preferably the elastic reservoir (11) has a common inlet/outlet that is connected to the tubings via a T-connection (13).

The outlet system (3) for exhaled air comprises tubings (14a,14b,14c) and a T-connection (15) that divides the outlet flow into two lines (14b,14c). One line (14c) leads a part of the exhaled air to the measuring unit (4). The other line (14b) takes care of excess air and leads it to ambient air (9). The flow designated to the measuring unit may be set in different ways. Most commercial NO detectors have a built in flow regulator for controlling the flow through the detector. In other alternatives, the outlet tubings (14a,14b,14c) may have one or more valves for regulating the partial flow going to the measuring unit (4), although it is important then to secure an even supply of exhaled air flow to the measuring unit (detector). The excess air may be led into ambient air via tubings (14b) of adequate length to avoid reversed flow and contamination from ambient air. To further secure that no contamination from ambient air enter the measuring unit (detector), the part of the exhaled breathing flow destinated to the measuring unit should be set clearly less than the average breathing flow rate e.g. above 5% and preferably below 50% of the average breathing flow rate. On the outlet tubings (14a,14c) going to the measuring unit (4, illustrated in FIG. 1b) or integrated with the measuring unit(4, illustrated in FIG. 1a), there may be one or more filters (16,17, 18) for the removal of substances present in exhaled air that may interfere with the measuring of NO. See below.

The measuring unit may comprise any method that gives the satisfactory sensitivity for measuring NO in air (from 1 p.p.b. and upwards). A commonly accepted technique is based on chemiluminescence and utilizes the light-emitting reaction:

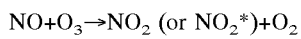

Approximately 20% of the $NO_2$ formed is obtained in the excited state ($NO_2^*$). During transition of $NO_2^*$ to $NO_2$ radiation is emitted (chemiluminescence), which is proportional to the NO concentration. $O_3$ is supplied in excess. See also Fontijn et al., Anal. Chem. 42 (1970) 575–79. The signal from the light-emitting reaction ($NO_2^*$ to $NO_2$) may be lowered by substances such as water and carbon dioxide. This means that in order to obtain absolute values these substances may be removed from the samples before measurement. This can be accomplished by letting the samples through filters for removal of substances interfering with the measuring operation (16 that is a filter for $H_2O$ and 17 that is a filter for $CO_2$). A second type of disturbing substances are particles which also may be removed by filters (18 that is a particle filter). Since the content of carbon dioxide and water is fairly constant in exhaled air, corresponding filters may be omitted leaving the particle filter (18) to be the most important one in the system of the present invention. Suitable detectors/instruments (19) for measuring NO are available on the market. See above. The system can be used either for continuous measurements over prolonged times (mixed air of several breaths) or for the measurements of NO in exhaled air of an individual breath (single breath analysis). The system also enables measurements of peak NO levels after regurgitation of air from the stomach. The use of the system according to the invention is given in the experimental part. See below. The system used in the experimental portion was at the priority date considered the most preferred one. During the priority year it has been realized that, for cases when orally exhaled air is to be sampled, mouth masks (mouth pieces) may be more convenient for the patient.

Diagnostic method

The method of the invention is a diagnostic method for finding mammals, preferably human individuals, suffering from inflammatory conditions (including risks therefore) in the airways. The method is characterized in that endogenously produced NO is measured in exhaled breathing air from a mammal, and that an abnormal level found is indicative of an inflammatory condition in the airways of the mammal.

For nasally exhaled air decreased NO levels have been found associated with acute inflammatory reactions causing severe nasal oedema and secretion, while increased NO levels have been found associated with low exposure of ambient inflammatory agents and/or a risk for nasal inflammation. Thus increased levels of NO during nasal breathing may be associated with both subclinical and clinical inflammatory conditions in the nasal mucosa. For orally exhaled air the lower range of increased NO levels may be indicative of subclinical inflammation in the lower airways and will thus be prognostic for the development of clinical inflammatory conditions, while the upper range is indicative of both acute and chronic inflammatory conditions in the lower airways. The NO levels in nasally and orally exhaled air should be compared to determine the relative contribution from the lower and upper airways, respectively.

The expressions "lower airways" and "upper airways" means below and above glottis, respectively.

When measuring NO in orally exhaled breathing air it is preferred that the patient inhales through the mouth. For nasally exhaled breathing air it is analogously preferred that the patient inhales through the nose.

MATERIAL AND METHODS

Study subjects: NO levels were measured in exhaled air of human subjects. The control subjects were non-smoking, healthy individuals, 27–52 years old and the asthmatics were non-smoking, atopic individuals, 33–45 years old with confirmed allergy towards at least rat allergen and occupational symptoms of mild asthma and rhinitis. The asthmatics were tested during non-symptomatic periods except in two cases (see below). Two of the asthmatics were inhaling a glucocorticoid (budesonide) regularly, two inhaled a $\beta_2$-agonist or cromoglycate when having symptoms and four did not take any medication. A group of subjects with allergic rhinitis, but not asthma, against birch pollen (n=9) was tested out of the pollen season during nasal breathing before and after nasal provocation with the allergen. In two other subjects with allergic rhinitis (birch pollen), but not asthma, oral breathing was tested out of the pollen season. In another subject with allergic rhinitis (birch pollen), but not asthma, oral and nasal breathing were tested immediately after the birch pollen season. All subjects were tested when they were subjectively free from respiratory infections, except in three cases of lower respiratory tract viral infections in control subjects. Exhaled NO was also measured at an intensive care unit in intubated and mechanically ventilated patients, without asthma. The study was approved by the local Ethical Committee.

Methods

A system was built as given in FIG. 1a, which allowed inhalation of NO-free (<1 p.p.b.) air from a gas tube and simultaneous and continuous measurement of NO in the exhaled air. No water or carbon dioxide filters were included because the contents of water and carbon dioxide in exhaled air were considered to be constant. A Berner valve was used as the air outlet valve (12).

When used, the system was rinsed with NO-free air (preferably <1 p.p.b. NO) by closing the face mask outlet and the outlet in the Berner valve, and by setting the air flow to 2 l/min. When the chemiluminescence NO reading was down to 1 p.p.b., the outlet in the face mask was unplugged and the face mask was quickly mounted over the nose and mouth of the test subject. The outlet of the Berner valve was then set to 2 cm $H_2O$ and the air flow adjusted to keep the elastic reservoir inflated to about ¾ of the maximal volume (6–8 l/min for adults). The test persons were allowed to breath freely in the face mask, either through the nose with the mouth closed or through the mouth using a nose clip. Breathing was allowed to continue until plateau levels of NO in exhaled air was noted (</=5 min in this system).

To evaluate the contribution from the nasal airways, an NO-free airstream (2–5 l/min) was introduced through one nostril of the control persons, while breathing through the mouth or holding the breath, and outlet air was sampled from the contra-lateral side. Similar measurements were made in the oral cavity, while holding the breath, with the inlet and outlet in different corners of the mouth. The level of NO and nitrogen dioxide ($NO_2$) on the outlet side was measured by continuous sampling at 0.7 l/min via Teflon tubings into an $NO/NO_x$ chemilumiscence analyzer (Eco Physics, Basel, Switzerland; see also Fontijn et al., Anal. Chem. 42 (1970) 575–79). $NO_x$ was measured after conversion of $NO_2$ to NO using a molybdenum thermal converter (Eco Physics) and the $NO_2$ concentration was calculated by the formula: $[NO_2]=[NO_x]-[NO]$.

RESULTS

When healthy control subjects were breathing through the mouth or the nose, much higher levels of NO were noted during nasal breathing (23±2 p.p.b.) compared to oral breathing (9±1 p.p.b.) (FIG. 2). Plateau levels of NO were reached within 4 minutes in this system, and no further changes were seen within a total of 10 minutes. Ventilation of the nasal airways with an airstream 2 l/min resulted in very high levels of NO on the outlet side (FIG. 2). These levels were further increased if the subjects were holding their breath with the mouth closed and thus forcing all air from one nasal cavity to the other via the nasopharynx. In contrast, similar measurements in the oral cavity resulted in low plateau levels of NO (</=4 p.p.b., n=5). Also very low plateau levels of NO (</=3 p.p.b.) were noted on the outlet side in intubated and mechanically ventilated patients (n=5). Taken together, this suggests that the NO in exhaled air of normal subjects is mainly generated in the nasal mucosa. In some individuals, low levels of $NO_2$ (</=5 p.p.b.) were seen in exhaled air in the beginning of the measurement period. However, the exhaled $NO_2$ concentration decreased during breathing of $NO_2$-free air to reach basal levels (</=2 p.p.b.) within 5 min.

In a group of non-symptomatic atopic subjects with mild asthma and rhinitis the level of NO in exhaled air during oral breathing was 2–3 fold higher compared to control subjects (FIG. 3a). When comparing plateau levels, there was no overlap between controls (range 5–16 p.p.b., n=12) and asthmatics (range 21–31 p.p.b., n=8). After occupational exposure to allergen, causing symptoms of bronchial obstruction, a further increase in exhaled NO (6–8 p.p.b.) was noted in 2 asthmatics not taking regular glucocorticoids. Furthermore, during episodes of lower respiratory tract infections in control subjects, causing cough and tracheobronchial soreness, elevated levels of NO in exhaled air during oral breathing were noted (11±2 p.p.b. before, 32±4 p.p.b. during and 16±1 p.p.b. after the symptomatic period, n=3). During nasal breathing, on the other hand, no significant elevation of NO levels in exhaled air was noted in asthmatics (FIG. 3b) and during lower respiratory tract infections (not shown), although a trend towards elevated levels was noted. In patients with allergic rhinitis (n=9), basal plateau levels of NO in exhaled air daring nasal breathing was close to the levels in control subjects (21+2 p.p.b.) when tested out of season. However, 2 minutes after nasal provocation with allergen, the plateau levels of NO were slightly reduced to 17±2 p.p.b. This reduction persisted for 15 min, but 24 hours later the NO levels in exhaled air during nasal breathing in these subjects were back to base line. In two other subjects with allergic rhinitis (birch pollen) oral breathing was tested. Elevated plateau levels of NO (21 and 23 p.p.b., respectively) compared to non-allergic controls were noted in these subjects. In another subject with allergic rhinitis (birch pollen) both oral and nasal breathing was tested immediately after the birch pollen season. In this subject an increased plateau level of NO during nasal breathing (40 p.p.b.) compared to controls (range 16–29 p.p.b.) was noted. During oral breathing this subject had a low plateau level (11 p.p.b.), however.

DISCUSSION

Basal production of NO in the human airways, as detected in exhaled air, seems to be restricted to the nasal mucosa. The precise source of NO remains unclear, but could be endothelial cells (Moncada S. et al., Pharmacol. Rev. 43 (1991) 109–142) or parasympathetic nerves (Kummer W. et al., Neuroreport 3 (1992) 653–655). This would fit with the apparently much lower basal levels of NO generated in the lower airways, since both vascularization and parasympathetic innervation are less in tracheobronchial mucosa compared to the nasal mucosa (Lundberg J.M. et al., In Bj örklund et al., (eds.), Handbook of Chemical Neuroanatomy, vol 6: The peripheral Nervous system. Amsterdam, Elsevier, 1988 391–444). The higher levels of NO noted during oral breathing compared to what was detected in intubated subjects, may represent NO derived from the nasopharyngeal mucosa. The transient presence of $NO_2$ in exhaled air may be interpreted as clearance of $NO_2$ that had been absorbed from ambient air ($NO_2$ concentrations between 5–20 p.p.b.) before the start of breathing $NO_2$-free air. The finding that the exhaled NO levels during nasal breathing in subjects with both allergic asthma and rhinitis were not significantly increased may reflect lower levels of inducible NO synthase in luminal structures of the nasal airways. An alternative explanation could be that the permeability for NO in inflamed nasal mucosa is reduced due to secretion, oedema and/or hyperemia, resulting in decreased passage of NO from deeper structures, such as endothelium and parasympathetic nerves, out into the lumen. This could possibly mask an increased production of NO in luminal structures of the nasal mucosa when measured in exhaled air. This notion is supported by the fact that acute exposure of allergen to the nasal mucosa results in reduced levels of exhaled NO during nasal breathing, while acute exposure of the bronchial mucosa results in increased levels of NO during oral breathing. However, the finding that the NO level in exhaled air during nasal breathing was enhanced after pollen season indicates the induction of NO synthase in luminal structures after long-term, low dose exposure of the allergen. Oral breathing in subjects with allergic rhinitis, but not asthma, resulted in elevated levels of NO in two out of three subjects. The two subjects with elevated levels complained about laryngeal symptoms during exposure of allergen, whereas the subject with non-elevated levels did not. This indicates that increased levels of NO in exhaled air during oral breathing could predict future development of asthma.

EXPERIMENTAL PART ADDED DURING THE PRIORITY YEAR

A first series of experiments was performed in order to check whether nitric oxide (NO) produced in the stomach contributed to the levels found in exhaled air.

Materials and methods

Subjects: The studied subjects were 4 healthy non-smoking individuals, 29–40 years old, and 4 non-smoking atopic individuals, 30–40 years old, with confirmed allergy towards at least rat allergen, and occupational symptoms of mild asthma and rhinitis. One of the asthmatics was inhaling a glucocorticoid (budesonide) regularly and the other 3 inhaled a beta-2 agonist or sodium cromoglycate when having symptoms. All subjects were tested when they were subjectively free from respiratory tract infections.

NO levels in regurgitated air from the stomach: Voluntary regurgitation of air was performed 3–5 min after intake of 30 cl carbonated water, pH 5.5 (Ramlösa®, Pripps AB, Sweden). Regurgitated air was led into a Teflon tubing system from which air was continuously sampled (0.8 l/min) into a NO chemiluminescence analyser (CLD 700; Eco Physics, Switzerland), and peak levels of NO were registered during otherwise normal breathing. Measurements of NO in regurgitated air from the stomach were made after 10 hours of fasting in combination with one of the following pretreatment procedures:

1. No pretreatment (control).
2. Intake of 50 g of iceberg lettuce (nitrate load).
3. Pretreatment per orally with a total of 240 mg of the proton pump inhibitor omeprazole (Astra-Hässle AB, Gothenburg, Sweden) distributed over a 24 h period prior to the experiments, and
4. Intake of 50 g of lettuce after omeprazole pretreatment.

NO levels in exhaled breathing air: The subjects were breathing NO-free air (NO<2 p.p.b.) with normal tidal volumes through a mouth piece connected to a non-rebreathing valve while wearing a nose clip. Exhaled air was led into a Teflon tubing system from which air was continuously sampled (0.8 l/min) and steady state levels of No were recorded. NO measurements were made after 10 h of fasting with and without omeprazole pretreatment.

Also, healthy subjects and patients with known gastro-oesophagal reflux and withdrawn medication were allowed to breath in a face mask while wearing a nose clip, both sitting upright and in a supine position. Swallows were registered.

Results: Control NO levels after 10 h of fasting in regurgitated air were 602±102 p.p.b. and these levels increased 4-fold after intake of lettuce. Pretreatment with omeprazole reduced the NO levels in regurgitated air both without and with intake of lettuce (95% and 75%, respectively). After 10 h of fasting, steady state levels of NO in exhaled air during normal tidal breathing were 4+1 p.p.b. (n=4) and 14±1 p.p.b. (n=4) in healthy subjects and asthmatics, respectively (p<0.05).

Omeprazole pretreatment did not significantly alter these levels in any group. In vitro experiments showed that within the pH range 0.9–2.5 the formation of NO was increased when acidity was increased in chewed lettuce as well as saliva alone.

Occasional, rapid peaks in NO levels (3–4 fold increases compared to basal levels) were noted during oral breathing in the supine position in both healthy subjects and patients with gastro-oesophagal reflux. The NO peaks were always related to swallows in the control subjects, whereas also several NO peaks unrelated to swallows were noted in the reflux patients.

Discussion: In this study we have identified the stomach as a major source of NO. Intragastric NO seems to be formed mainly non-enzymatically requiring an acidic environment, since inhibition of gastric acid secretion by omeprazole almost abolished NO in regurgitated air. This indicates that the NO level in regurgitated air reflects the pH in gastric juice. The levels of NO in regurgitated air were found to be approximately 100 times higher during fasting conditions and 400 times higher after nitrate intake, compared to the levels in exhaled air during normal tidal breathing through the mouth. However, the high NO level in the stomach does not seem to contribute continuously to the NO levels in exhaled air during normal breathing in healthy subjects or asthmatics since the NO levels in orally exhaled air were not affected by omeprazole pretreatment. These findings seem possible to use for the diagnosis of gastro-oesophagal reflux in a patient, with non-swallow-related NO-peaks being indicative of gastro-oesophagal reflux, and with the measurement preferably being performed on orally exhaled air with the patient in a horizontal position. Furthermore, NO levels in regurgitated air may be used to monitor treatment with drugs inhibiting gastric acid secretion.

Nasally derived NO.

A second series of experiments was performed in order to determine the exact origin and significance of nasally derived NO.

Materials and Methods: Air was sampled directly into a syringe either from the nasal cavity or from one maxillary sinus via a perforation (autoinjecting needle) through the nasal wall in 3 healthy volunteers. Air samples were directly injected into the NO analyzer and peak levels were registered. Mucosal biopsies from the nasal cavity and maxillary sinus were taken in patients undergoing surgery and the presence of different NO synthases was examined by immunohistochemical technique using specific monoclonal antibodies. Exhaled NO levels were also measured in patients with Kartagener's syndrome (n=4).

Results: Much higher levels of NO were seen in air collected from the maxillary sinus (3000–4000 p.p.b.) compared to air from the nasal cavity (200–300 p.p.b.). In accordance, high expression of the inducible form of NO synthase was detected by immunohistochemistry in epithelial cells from the maxillary sinus but not from the nasal cavity. In patients with Kartagener's syndrome, close to zero levels of exhaled No was found during both oral and nasal breathing.

Discussion: The inducible NO synthase seems to be constitutively expressed in the epithelium of human nasal sinuses and is apparently very active. The high luminal concentrations of No in the nasal sinuses may be an important component of the primary, unspecific host defence, since NO in high concentrations has been shown to be bacteriostatic (Moncada S et al., Pharmacol. Rev. 43 (1991) 109–42), and the nasal sinuses are normally sterile in contrast to the nasal cavity. Low nasal levels of NO may thus be indicative of airway epithelial diseases like Kartagener's syndrome and increased susceptibility for developing sinusitis.

We claim:

1. A system for separate measurement of endogenously produced NO in nasally or orally exhaled air, comprising:
   (i) a face mask comprising a mouth piece and/or a nose piece, and which face mask covers the nose and/or mouth of the individual that the mask is intended to be used on;
   (ii) an inlet unit for inhaled breathing air connected to one of said mouth piece or said nose piece;
   (iii) an outlet unit for exhaled breathing air connected to one of said mouth piece or said nose piece;
   (iv) a non-rebreathing valve connecting said inlet and outlet units, through which inhaled and exhaled breathing air, respectively, passes;
   (v) a flow regulator, through which the exhaled air passes; and
   (vi) a measuring unit for endogenously produced NO connected to said outlet unit for measuring endogenously produced NO in nasally exhaled air or in orally exhaled air.

2. The system according to claim 1, wherein said inlet unit for inhaled breathing air comprises tubing having an opening to ambient air, said tubing being equipped with a filter for removal of NO present in ambient air.

3. The system according to claim 1, wherein said inlet unit for inhaled breathing air comprises tubing connected to a pressurized container for breathing air, which contains nonsignificant levels of NO.

4. The system according to claim 3, wherein an elastic reservoir is connected to the tubing between the pressurized container and the non-rebreathing valve.

5. The system according to any one of claims 2–4, wherein said outlet unit has cubing for exhaled breathing air comprising a T-connection for diverting sample flow air, which is a cart of the exhaled breathing air to the measuring unit.

6. The system according to claim 5, wherein said sample air flow is less than an average breathing flow rate (minute volume) of the individual to whom the system is intended to be applied so that contamination by ambient air is avoided.

7. The system according to any one of claims 2–4, wherein at least one filter selected from the group consisting of:
   (i) a filter for drying exhaled air;
   (ii) a filter for the removal of $CO_2$ in exhaled breathing air; and
   (iii) a particle filter is connected to the tubing or situated in the outlet unit or integrated with the measuring unit, with the provision that the filter or filters are so placed that air targeting the detector will pass said at least one filter before entering the detector.

8. The system according to any one of claims 2–4 further comprising at least one device selected from the group consisting of:
   (i) a flow meter; and
   (ii) an outlet valve preventing
      (a) the build up of pressure in the tubing for inhaled breathing air, and
      (b) the leakage of air from the inlet unit to the outlet unit via the non-rebreathing valve.

9. A system for measurement of NO in exhaled air, comprising:
   (i) a face mask that covers the nose and/or mouth of the individual that the mask is intended to be used on;
   (ii) a nasal or oral inlet unit for inhaled breathing air;
   (iii) a nasal or oral outlet unit for exhaled breathing air; wherein if said inlet unit is nasal, said outlet unit is nasal, and if said inlet unit is oral, said outlet unit is oral;
   (iv) a non-rebreathing valve through which inhaled and exhaled breathing air passes; and
   (v) a measuring unit for NO connected to said outlet unit.

10. A method for diagnosis of inflammatory conditions in airways of humans, comprising:
    separately measuring endogenously produced NO in nasally exhaled air or in orally exhaled air with a system according to any one of claims 2–4 and 9.

11. A method for diagnosis of inflammatory conditions in the airways of humans, comprising:
    measuring endogenously produced NO in nasally exhaled air to obtain a measured value for endogenously produced NO in said nasally exhaled air;
    comparing the measured value against a reference value based on values typical for healthy individuals; and
    diagnosing a level higher than values typical for healthy individuals as an indication of an inflammatory condition in the upper airways.

12. The method according to claim 11, wherein said inflammatory condition is rhinitis.

13. A method for diagnosis of inflammatory conditions in airways of humans, comprising:
    measuring the level of NO in nasally exhaled air to obtain a measured value for endogenously produced NO in said nasally exhaled air; and
    comparing the measured value against a reference value based an values typical for healthy individuals, wherein a level lower than values typical for healthy individuals is taken as an indication of an acute inflammation in the upper airways.

14. The method according to claim 13, further comprising diagnosing an airway epithelial disease or increased susceptibility for developing sinusitis.

15. The method of claim 14, wherein said epithelial disease is Kartagener's syndrome.

16. A method for diagnosis of inflammatory conditions in an airway of a human having a mouth, a nasal cavity, an upper airway and a lower airway, comprising:
    inhaling through the mouth of said human when an indication of the condition of the lower airways is desired and determining the level of NO in orally exhaled air, and when an indication of the condition of the upper airways is desired, determining the level of NO in nasally exhaled air or in an air sample taken from the nasal cavity.

17. A method for diagnosis of inflammatory conditions in upper airways of a human having a mouth, a nasal cavity, and upper airway and a lower airway, comprising:

taking a gas sample from the nasal cavity; and determining the level of NO in said sample, wherein a level higher than values typical for healthy individuals is taken as an indication of an inflammatory condition in the upper airways.

18. A method for diagnosis of inflammatory conditions in upper airways of a human having a mouth, a nasal cavity, and upper airway and a lower airway, comprising:

taking an air sample from the nasal cavity; and determining the level of NO in said sample wherein a level lower than values typical for healthy individuals is taken as an indication of an acute inflammation in the upper airways.

19. The method according to claim 16, for the diagnosis of airway epithelial diseases.

20. The method according to any one of claims 17–19, wherein the gas sample taken from the nasal cavity is a sample aspirated from the nasal cavity or a sample obtained by flushing the nasal cavity with NO-free air.

21. A method for the diagnosis of inflammatory conditions in airways of a human patient having a nasal cavity, comprising:

taking a gas sample from the nasal cavity of the patient while the patient is holding his/her breath; and determining the level of NO in said gas sample in order to perform the diagnosis of inflammatory conditions in the airways.

22. A method for diagnosis of inflammatory conditions in airways of a human having a nasal cavity, comprising:

exhaling orally against a flow-regulator while a sample is taken from the nasal cavity; and determining the level of NO in said sample in order to perform the diagnosis of inflammatory conditions in the airways.

23. A method for diagnosis of inflammatory conditions in the airways of a human having lower and upper airways, comprising:

determining the level of NO in nasally exhaled air;

determining the level of NO in orally exhaled air;

comparing said level of NO determined in nasally exhaled air to the level of NO determined in orally exhaled air; and determining the relative contribution of NO from the lower and upper airways, respectively.

24. The method according to any one of claims 11–16, comprising determining the level of NO in nasally exhales air, determining the level of NO in orally exhaled air and determining relative contributions of NO from the lower and upper airways, respectively.

25. A method for diagnosis of inflammatory conditions in the airways of humans, comprising:

passing exhaled breathing air, which is nasally exhaled air or which is orally exhaled air, through at least one filter selected from the group consisting of:
(i) a filter for drying exhaled air;
(ii) a filter for the removal of $CO_2$ in exhaled breathing air; and
iii) a particle filter; and thereafter measuring the amount of NO in said exhaled breathing air which has been passed through said filter.

26. A method for diagnosis of gastro-esophageal disorders in humans, comprising:

determining the level of NO in regurgitated air and taking an altered level of NO in relation to a level typical for a healthy population as an indication of a disease associated with altered levels of NO production.

27. A method for diagnosis of gastric reflux in humans, comprising;

determining the level of NO in breathing air, over a predetermined period of time, wherein an occurrence of peak NO levels, compared to a baseline level during said period of tire, is taken as an indication of gastric reflux.

28. A method for monitoring effects of treatment with drugs inhibiting gastric acid secretion, comprising:

administering a drug to a subject; and determining the level of NO in regurgitated air of said subject after administration of said drug.

29. The method according to claim 17, wherein said inflammatory condition in the upper airways is rhinitis.

30. The method according to claim 19, wherein the airway epithelial disease is Kartagener's syndrome or increased susceptibility for developing sinusitis.

31. The method according to claim 27, which further comprises the steps of:

subjecting said human to fasting conditions to establish said baseline level; and administering a substance which affects gastric reflux to said human.

32. The method according to claim 31, wherein said substance which affects gastric reflux is food.

33. The method according to claim 32, wherein said substance which affects gastric reflux is a drug.

34. The system according to claim 1, wherein said inlet unit and said outlet unit are connected to the same one of said mouth piece and said nose piece.

35. A method for diagnosis of inflammatory conditions in lower airways of humans, comprising:

causing a patient to inhale orally through the mouth and thereafter causing said patient to exhale orally through the mouth; and measuring endogenously produced NO in said orally exhaled air with a system comprising:
(i) a mouth piece;
(ii) an inlet unit for inhaled breathing air connected to said
(iii) an outlet unit for exhaled breathing air connected to said mouth piece;
(iv) a flow regulator, through which the exhaled air passes; and
(v) a measuring unit for endogenously produced NO connected to said outlet unit for measuring endogenously produced NO in orally exhaled air.

36. The method of claim 35, wherein said system further comprises a non-rebreathing valve connecting said inlet and outlet units through which inhaled and exhaled breathing air, respectively, passes.

37. A system for diagnosis of inflammatory conditions in lower airways of humans, comprising:
(i) a mouth piece through which a human can inhale and exhale;
(ii) an inlet unit for inhaled breathing air connected to said mouth piece,
(iii) an outlet unit for exhaled breathing air connected to said mouth piece;
(iv) a flow regulator, through which the exhaled air passes; and
(v) a measuring unit for endogenously produced NO connected to said outlet unit for measuring endogenously produced NO in orally exhaled air.

38. The system of claim 37, which further comprises a non-rebreathing valve connecting said inlet and outlet units through which inhaled and exhaled breathing air, respectively, passes.

* * * * *

UNITED STATES PATENT AND TRADEMARK OFFICE
CERTIFICATE OF CORRECTION

PATENT NO. : 5,922,610
APPLICATION NO. : 08/578653
DATED : July 13, 1999
INVENTOR(S) : Kjell Alving et al.

It is certified that error appears in the above-identified patent and that said Letters Patent is hereby corrected as shown below:

Col. 12, lines 28-45; should read;

A method for diagnosis of inflammatory conditions in lower airways of humans, comprising:
causing a patient to inhale orally through the mouth and thereafter causing said patient to exhale orally through the mouth; and
measuring endogenously produced NO in said orally exhaled air with a system comprising:
    (i) a mouth piece;
    (ii) an inlet unit for inhaled breathing air connected to said <u>mouth piece</u>
    (iii) an outlet unit for exhaled breathing air connected to said mouth piece;
    (iv) a flow regulator, through which the exhaled air passes; and
    (v) a measuring unit for endogenously produced NO connected to said outlet unit for measuring endogenously produced NO in orally exhaled air.

Signed and Sealed this

Twenty-sixth Day of May, 2009

JOHN DOLL
*Acting Director of the United States Patent and Trademark Office*